United States Patent [19]

Krause et al.

[11] Patent Number: 4,983,913
[45] Date of Patent: Jan. 8, 1991

[54] METHOD AND APPARATUS FOR MEASURING A GAS BY EXPLOITING THE PARAMAGNETIC PROPERTIES OF THE GAS

[75] Inventors: Hans Krause, Bad Nauheim; Rudi Roess, Bruchkoebel; Ulrich Modlinski, Alzenau-Albstadt, all of Fed. Rep. of Germany

[73] Assignee: Leybold Aktiengesellschaft, Fed. Rep. of Germany

[21] Appl. No.: 497,929

[22] Filed: Mar. 23, 1990

[30] Foreign Application Priority Data

Dec. 4, 1989 [DE] Fed. Rep. of Germany ....... 3940036

[51] Int. Cl.$^5$ ..................... G01N 31/00; G01N 27/74; G01R 33/12
[52] U.S. Cl. ..................................... 324/204; 73/25.02
[58] Field of Search .................. 324/204; 73/27 A

[56] References Cited

U.S. PATENT DOCUMENTS 2,744,234  5/1956  Munday et al. ................... 324/204
3,881,152  4/1975  Tasaki .
4,229,697  10/1980  Petrosky et al. .
4,772,848  9/1988  Hummel .

FOREIGN PATENT DOCUMENTS 903749  6/1953  Fed. Rep. of Germany .
947932  3/1956  Fed. Rep. of Germany .
2158715  11/1971  Fed. Rep. of Germany .
2196127  10/1987  United Kingdom .

OTHER PUBLICATIONS

"An Astatic Magnetometer with Negative Feedback", A. de Sa, J. Widdowson; Journal of Physics E., vol. 7, No. 4, pp. 266–268, Apr. 1974.

Primary Examiner—Walter E. Snow
Attorney, Agent, or Firm—Hill, Van Santen, Steadman & Simpson

[57] ABSTRACT

A paramagnetic gas measuring device/instrument including an infrared radiator for irradiating diamagnetic members of the device and for creating a climate within a measuring chamber suitable to evaporate moisture from the members and a gas being analyzed.

15 Claims, 1 Drawing Sheet

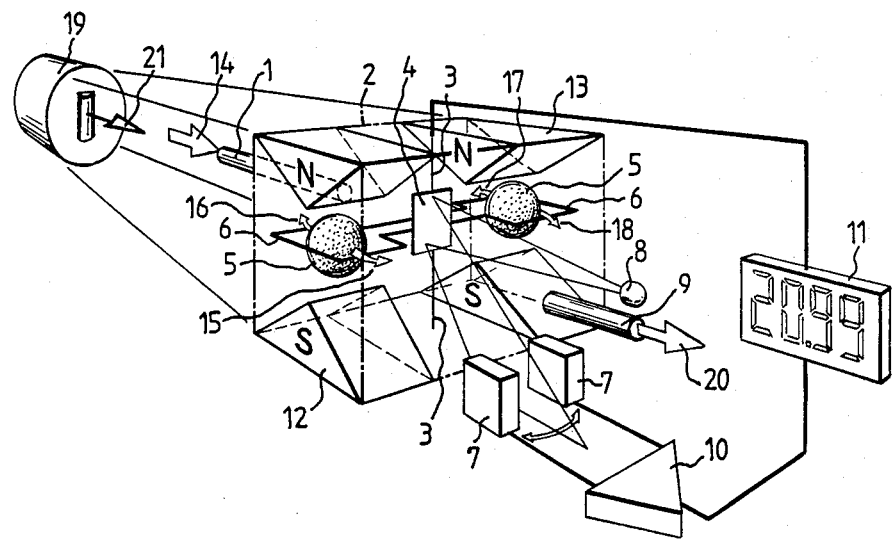

METHOD AND APPARATUS FOR MEASURING A GAS BY EXPLOITING THE PARAMAGNETIC PROPERTIES OF THE GAS

BACKGROUND OF THE INVENTION

The invention generally is directed to methods and apparatus for measuring the presence and/or concentration of a gas, e.g., oxygen, by exploiting the paramagnetic properties of the gas and by employing at least one member that comprises a substance having diamagnetic properties on which a force is exerted, given the presence of the gas, due to the paramagnetic properties of the gas. More specifically, the invention is directed to paramagnetic gas/oxygen measuring devices/instruments.

The acquisition and interpretation of measurements of gases such as oxygen concentrations are necessary in various situations, for example, process control, operating analysis, environmental protection, as well as in research and development. Modern gas analyzers which are employed to obtain oxygen measurements generally are computer assisted instruments with extremely compact structures.

One such gas/oxygen analyzer is disclosed in a brochure provided by Leybold AG bearing the designation "Oxynos 100" and the number 43-520.01.

Another paramagnetic measuring instrument is disclosed in U.S. Pat. No. 4,772,848 the teachings of which are fully incorporated herein.

Further, various paramagnetic measuring devices having mechanical gas/oxygen measuring modules are known that output a deflection due to the presence of paramagnetic gases, the deflection in turn being transduced into an electrical signal related thereto.

However, the transverse sensitivity (i.e., an unwanted measuring sensitivity of a measuring module to a gas constituent that one does not want to measure) in the prior art devices can be greater than predicted in theory. Non-magnetic gases and particles as well as aerosols can have a considerable influence on the measurement. These influences are undesirable because they introduce inaccuracies in the measurement.

Prior art devices are also limited in that they are sensitive only down to a resolution of two percent oxygen by volume. Below this resolution of two volume percent oxygen, negative influences of water content of a damp gas are so great that fast precise measurements are not possible.

Further, chronologically slow transient effects can appear, these effects being capable of causing unwanted distortion. These transient effects include adsorption and absorption of water particles or water films that produce inaccuracies in the resulting measurements.

Attempts have been made to overcome the above-described limitations by thermostatically controlling the measuring cells. However, thermostat control of measuring cells has provided only a relatively slight improvement. Modern oxygen analyzers must be able to suppress transverse sensitivity to a greater degree to meet future demands.

SUMMARY OF THE INVENTION

The invention provides an improved method and apparatus for measuring a gas (e.g., oxygen) by exploiting the paramagnetic properties of the gas. A significant decrease in transverse sensitivity is provided.

To these ends, the invention provides that water that would otherwise introduce measurement inaccuracies is evaporated. Further, water adsorbates are selectively desorbed so that the analyzer temperature and the gas temperature are not significantly increased. As a result, measurement errors are considerably reduced.

Further, time related behavior of the apparatus is optimized such that measuring properties presently given dry measured gases is achieved.

Yet further, electrostatic influences that normally would introduce measurement inaccuracies, particularly due to the presence of water vapors, are reduced or eliminated. One example of such an electrostatic effect derives from water drops that apply themselves to a member that comprises a substance having diamagnetic properties. With respect to the device disclosed in the Leybold AG brochure, the water drops (or water films) apply themselves to balls of a dumbbell-like arrangement.

In an embodiment, the invention provides a paramagnetic measuring device/instrument including an infrared radiator operatively positioned to irradiate members comprising a diamagnetic substance.

In another embodiment, the invention provides a method for measuring the presence of oxygen by exploiting the paramagnetic properties of a gas being analyzed such as oxygen wherein two members containing a diamagnetic substance, preferably nitrogen, are arranged dumbbell-like relative to each other. In the method, a force is exerted due to the presence of the gas such that the members are provided with a torque about a common axis of rotation extending between the members. The torque is compensated by a magnetic field generated by a current permeated wire loop. The intensity of the current required to compensate the torque is employed as a direct measure of gas/oxygen concentration. The members are irradiated with infrared radiation to eliminate moisture influences.

An advantage of the invention is that water adsorbate layers can be selectively desorbed without significantly increasing the temperatures of components of a paramagnetic gas analyzer or the gas.

Another advantage of the invention is the provision of a method and means for evaporating moisture in a gas being analyzed.

Yet another advantage of the invention is that the chronological behavior of a paramagnetic gas measuring device is improved, the measuring achieving that quality usually encountered given moisture free gases.

These and other features and advantages of the invention will become apparent with reference to the following detailed description of the presently preferred embodiments and accompanying drawing.

BRIEF DESCRIPTION OF THE DRAWING

The sole FIGURE is a combination of a schematic and perspective view of a measuring module of a paramagnetic gas measuring device embodying principles of the invention.

DETAILED DESCRIPTION OF THE INVENTION

A paramagnetic gas measuring device/instrument is depicted in the sole FIGURE in such a manner that the physical characteristics and principles of use thereof should be apparent thereof in view of the following description. Further reference can be made to the Leybold AG brochure, the disclosure of which is fully incorporated herein to the extent permitted.

In the illustrated device, a gas to be analyzed is introduced into a measuring chamber 2 of the device via an admission line/conduit 1. The gas is exhausted from the chamber 2 via a suitable line/conduit 9. Preferably, the gas is oxygen.

Within the chamber 2 is suspended a wire 3, preferably constructed of stretched platinum. The wire 3 is suspended from a ceiling so that is extends perpendicularly therefrom. Preferably, the wire 3 is secured to a central portion of the ceiling.

Secured to the wire 3 along the length thereof is a rectangular mirror 4. The mirror 4 is capable of reflecting light directed thereon. The mirror 4 is illustrated as being positioned at about a midpoint of the wire 3.

Two crystal balls 5 are positioned dumbbell-like on opposite sides of the wire 3 and are operatively suspended from the wire 3 by means of a wire loop 6. The loop 6 extends around the balls 5 and is attached at a backside of the mirror 3 and substantially resembles a dumbbell shape.

Due to the nature of the wire 3, the balls 5 are suspended such that they can substantially freely rotate about an axis defined by the wire 3. Of course, excessive rotation can cause the wire 3 to twist. This twisting induces torque forces that can counter the rotation of the balls 5.

The balls 5 are filled with a substance having diamagnetic properties. Preferably, this substance is nitrogen.

Photodetectors 7 are operatively positioned away from the mirror 4 and adjacent a floor of the chamber 2 so that a light beam footprint generated by a light source 8 can be detected when reflected by the mirror 4. The light source 8 is operatively positioned substantially in-line with the mirror 4.

It can be appreciated that rotation of the balls 5 will cause rotation of the mirror 4. The rotation of the mirror will, in turn, cause changing of the position of the reflected light beam which is detected by the photodetectors 7. Thus the photodetectors 7 can be employed to detect rotation of the balls 5.

Coupled to the photodetector 7 is an amplifier 10 that produces a variable output depending upon which photodetector receives the greatest amount of reflected light. The amplifier 10 has an output coupled to suitable indicating means such as an electronic display.

As further illustrated, relatively strong permanent magnets 12 and 13 are operatively positioned above and below the crystal balls 5 so as to generate a non-uniform magnetic field outside of the measuring chamber 2.

When gas molecules, such as oxygen molecules, are introduced into the chamber 2 via the line/conduit 1 as indicated by arrow 14, a force is exerted on the balls 5 filled with the diamagnetic substance, as is known. This force is a torque that causes the balls to rotate and, consequently, the mirror 4 to rotate out of their quiescent position. This rotation is indicated by arrows 15, 16, 17, and 18. As discussed previously, this, in turn, causes deflection of the light beam reflected from the mirror 4.

An electrical current introduced into the wire 6 creates a magnetic field that opposes rotation of the balls 5 and thus compensates for rotational motion of the balls 5. the amount of current required to fully compensate for the rotational movement of the balls 5 is related to the amount of gas/oxygen being analyzed. Thus, measurement of the current required to produce no deflection in the reflected light beam can be a measure of the concentration of the gas, preferably oxygen, being analyzed.

In accordance with the invention, the crystal balls 5 and the atmosphere within the chamber 2 are irradiated with infrared radiation by means of an infrared radiator 19 operatively positioned outside of one side of the chamber 2. In the FIGURE, the radiator 19 is positioned substantially in-line with the line 1 and perpendicular to a line extending between the balls 5 in their quiescent state. The radiator 19 selectively desorbs the water adsorbate layers, films, and drops on the balls 5 preferably by heating at least the surface of the balls to about 500° to about 770° C. An arrow 21 indicates the direction of the infrared radiation.

It can be appreciated that the temperatures of the other components of the measuring cell and the gas are elevated insignificantly. However, moisture is caused to be evaporated and the vapors to be exhausted with exiting gas via the exhaust line/conduit 9 in the direction indicated by arrow 20.

While a preferred embodiment has been shown, modifications and changes may become apparent to those skilled in the art which shall fall within the spirit and scope of the invention. It is intended that such modifications and changes be covered by the attached claims.

We claim:

1. A paramagnetic gas measuring device including diamagnetic members, and an infrared radiator operatively positioned to irradiate the members so as to desorb moisture adsorbed thereon.

2. The device of claim 1, wherein the gas to be analyzed is oxygen.

3. The device of claim 1, wherein the members comprise crystal balls tilled with nitrogen.

4. The device of claim 1, including a measuring chamber within which the gas is analyzed and within which the members are positioned, the infrared radiator being positioned so as to heat the members to between about 500° and 770° C.

5. In a method for measuring the presence of oxygen via paramagnetic analysis, comprising the steps of:
   providing at least one diamagnetic member;
   exposing the member to a gas; and
   irradiating the member with infrared radiation.

6. The method of claim 5, wherein the gas is oxygen.

7. The method of claim 5, wherein the step of providing at least one diamagnetic member comprises providing a paramagnetic gas analyzer.

8. The method of claim 5, wherein the step of irradiation of the member includes irradiating an atmosphere surrounding the member.

9. The method of claim 8, wherein the step of irradiating comprises irradiating the member until it attains a surface temperature of about 500° to about 770° C.

10. In a method for measuring the presence of oxygen via paramagnetic analysis the step of:
   providing at least two diamagnetic members rotatably positioned on opposite sides of a common axis;
   said member having a quiescent state position;
   exposing the members to a gas;
   permitting rotation of the members in response to diamagnetic force exerted thereon by the presence of oxygen; such rotation by introducing an electrical current in a loop;
   correlating an intensity of the current required to return the members to their quiescent state position with a concentration of oxygen present in the gas; and irradiating the members with infrared radiation to remove water collected in or on said members.

11. The method of claim 10, wherein the members are positioned within a chamber having a gas inlet and a gas outlet.

12. The method of claim 10, wherein said chamber is irradiated with an infrared radiator, yet only said members a significant increase in temperature.

13. The method of claim 10, wherein said chamber is irradiated so that said members are heated to a temperature ranging from about 500° to about 770° C.

14. A device for measuring a gas concentration comprising:

a chamber having a gas inlet and a gas outlet;

a pair of diamagnetic members containing a diamagnetic substance suspended within the chamber for free rotation about a common axis;

a magnet member operatively shaped and positioned above and below the diamagnetic members to generate a non-uniform magnetic field outside of the chamber;

an electrical conductor operatively looped about the diamagnetic members to generate a magnetic field thereabout that counteracts any torque force resulting from introduction of a gas into the chamber, the intensity of the current required to generate a magnetic field that fully counteracts a torque correlating to a concentration of the gas; and an infrared radiator operatively positioned to irradiate the diamagnetic members.

15. The device of claim 14, wherein the torque generating gas is oxygen.

* * * * *